(12) United States Patent
Du-Thumm et al.

(10) Patent No.: US 9,119,879 B2
(45) Date of Patent: Sep. 1, 2015

(54) ORAL CARE COMPOSITIONS COMPRISING A QUINONE AND A FURTHER ANTIMICROBIAL AGENT

(75) Inventors: Laurence Du-Thumm, Princeton, NJ (US); Lyndsay Schaeffer-Korbylo, Flemington, NJ (US); David Santos, Edison, NJ (US); Stanislav Jaracz, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 39 days.

(21) Appl. No.: 13/992,338

(22) PCT Filed: Dec. 7, 2010

(86) PCT No.: PCT/US2010/059160
§ 371 (c)(1),
(2), (4) Date: Jun. 7, 2013

(87) PCT Pub. No.: WO2012/078135
PCT Pub. Date: Jun. 14, 2012

(65) Prior Publication Data
US 2013/0272972 A1    Oct. 17, 2013

(51) Int. Cl.
| | |
|---|---|
| A61K 31/122 | (2006.01) |
| A61K 45/06 | (2006.01) |
| A61K 9/00 | (2006.01) |
| A61K 9/06 | (2006.01) |
| A61K 9/08 | (2006.01) |
| A61K 31/047 | (2006.01) |
| A61K 31/055 | (2006.01) |
| A61K 31/085 | (2006.01) |
| A61K 31/14 | (2006.01) |
| A61K 33/24 | (2006.01) |
| A61K 33/30 | (2006.01) |
| A61K 47/02 | (2006.01) |
| A61K 47/10 | (2006.01) |
| A61K 47/14 | (2006.01) |
| A61K 47/26 | (2006.01) |
| A61K 8/27 | (2006.01) |
| A61K 8/34 | (2006.01) |
| A61K 8/35 | (2006.01) |
| A61Q 11/00 | (2006.01) |
| A61K 8/03 | (2006.01) |

(52) U.S. Cl.
CPC . *A61K 45/06* (2013.01); *A61K 8/03* (2013.01); *A61K 8/27* (2013.01); *A61K 8/347* (2013.01); *A61K 8/355* (2013.01); *A61K 9/0053* (2013.01); *A61K 9/06* (2013.01); *A61K 9/08* (2013.01); *A61K 31/047* (2013.01); *A61K 31/055* (2013.01); *A61K 31/085* (2013.01); *A61K 31/122* (2013.01); *A61K 31/14* (2013.01); *A61K 33/24* (2013.01); *A61K 33/30* (2013.01); *A61K 47/02* (2013.01); *A61K 47/10* (2013.01); *A61K 47/14* (2013.01); *A61K 47/26* (2013.01); *A61Q 11/00* (2013.01)

(58) Field of Classification Search
USPC .................................................. 424/59, 422
See application file for complete search history.

(56) References Cited

U.S. PATENT DOCUMENTS

| | | | |
|---|---|---|---|
| 5,776,435 | A | 7/1998 | Gaffar et al. |
| 6,355,229 | B1 | 3/2002 | Adamy |
| 2003/0108576 | A1 | 6/2003 | Bielli |
| 2004/0086575 | A1 | 5/2004 | Smith |
| 2004/0241109 | A1 | 12/2004 | Parikh |
| 2009/0220625 | A1 | 9/2009 | Herrmann et al. |
| 2009/0246292 | A1 | 10/2009 | Seville et al. |
| 2009/0306218 | A1 | 12/2009 | Fitzgerald et al. |

FOREIGN PATENT DOCUMENTS

| | | |
|---|---|---|
| CA | 2774961 | 8/2005 |
| DE | 4434312 | 3/1996 |
| GB | 2455625 | 6/2009 |
| JP | 2009-001497 A | 1/2009 |
| WO | WO 02/02128 | 1/2002 |
| WO | WO 2006/124989 | 11/2006 |
| WO | WO 2008/035078 | 3/2008 |
| WO | WO 2009/074792 | 6/2009 |
| WO | WO 2009/148875 | 12/2009 |

OTHER PUBLICATIONS

International Search Report and Written Opinion in International Application No. PCT/US10/059160, mailed Jul. 4, 2011.
Written Opinion in International Application No. PCT/US10/059160, mailed Nov. 6, 2012.
Tchaou et al., 1995, "In vitro inhibition of bacteria from root canals of primary teeth by various dental materials," Pediatric Dentistry 17(5):351-355.

*Primary Examiner* — Walter Webb
(74) *Attorney, Agent, or Firm* — Howard C. Lee

(57) ABSTRACT

Described herein are compositions comprising a quinone and one or more antibacterial agents, and methods of preparing and using the same.

15 Claims, No Drawings

ORAL CARE COMPOSITIONS COMPRISING A QUINONE AND A FURTHER ANTIMICROBIAL AGENT

BACKGROUND

Tert-butylhydroquinone (TBHQ) has been used as a preservative for unsaturated vegetable oils and edible animal fats. It has also been used industrially as a stabilizer to inhibit autopolymerization of organic peroxides.

SUMMARY

In some embodiments, the present invention provides a composition comprising: a quinone selected from the group consisting of alkyl-substituted benzoquinones, halo-substituted benzoquinones, alkyl-substituted hydroquinones and halo-substituted hydroquinones; and one or more antimicrobial agents selected from the group consisting of a zinc containing compound, a tin containing compound, tetrahydrocurcumin, a quaternary ammonium compound, a chlorophenol, and a combination of two or more thereof; wherein the quinone is provided in an amount effective to provide a synergistic increase in antimicrobial activity. In some embodiments, the quinone is tert-butylhydroquinone (TBHQ).

In some embodiments, the present invention provides methods for treating a disease or condition of the oral cavity comprising applying a composition as described herein to an oral cavity surface of a subject in need thereof.

In some embodiments, the invention provides a method of reducing the presence of microorganisms in the oral cavity of a subject in need thereof, the method comprising administering to an oral cavity surface of the subject an effective amount of any of the compositions described herein.

Some embodiments provide for the use of a composition as described herein for the manufacture of a medicament for treating a disease or condition of the oral cavity.

DETAILED DESCRIPTION

Unless otherwise specified, all percentages and amounts expressed herein and elsewhere in the specification should be understood to refer to percentages by weight. The amounts given are based on the active weight of the material.

The antimicrobial activity of quinones, for example TBHQ, is 20 to 60 times lower than known antimicrobial agents, for example, triclosan and cetylpyridinium chloride ("CPC"), respectively. The MIC of TBHQ against three common pathogens is shown in Table 1.

TABLE 1

Minimum inhibitory concentration of TBHQ

| Bacterium | MIC |
| --- | --- |
| A. viscosus | 62.5 ppm |
| P. gingivalis | 62.5 ppm |
| F. nucleatum | 62.5 ppm |

However, the present inventors have found that combining a quinone with one or more antibacterial agents can provide a combination that provides a synergistic increase in antimicrobial activity.

As used herein, the phrase "synergistic increase in antimicrobial activity" refers to an increase in antimicrobial activity that is greater than the additive effect that would be expected from the combination of two or more agents, in view of the antimicrobial activity demonstrated by the agents independently. In some embodiments, a synergistic increase in antimicrobial activity may be manifested, for example, by a lower concentration of the compound(s) being needed to inhibit and/or to kill the relevant organism, and/or by a larger zone of inhibition in a disc diffusion assay, and/or by a faster rate of microbial inhibition or killing.

In some embodiments, the present invention provides compositions comprising: a quinone selected from the group consisting of alkyl-substituted benzoquinones, halo-substituted benzoquinones, alkyl-substituted hydroquinones and halo-substituted hydroquinones; and one or more antimicrobial agents selected from the group consisting of a zinc containing compound, a tin containing compound, tetrahydrocurcumin, a quaternary ammonium compound, a chlorophenol, and a combination of two or more thereof; wherein the quinone is provided in an amount effective to provide a synergistic increase in antimicrobial activity.

In further embodiments, at least one of said one or more antimicrobial agents is selected from the group consisting of zinc citrate, zinc oxide, stannous chloride, tetrahydrocurcumin, cetylpyridinium chloride and triclosan. In other embodiments, at least one of said one or more antimicrobial agents is present at a concentration of from about 0.025 ppm to about 100 ppm. In some embodiments, the quinone is TBHQ.

In some embodiments, the composition is an oral care composition. In some embodiments, the oral compositions of the present invention may be in the form of a mouthwash, a gargle, a dentifrice, an anti-plaque composition or a general antiseptic composition, for example, in the form of a denture cleansing tablet or solution. In some embodiments, the compositions of the present invention are in the form of a semi-solid or solid such as a toothpaste, a gel dentifrice, a dental powder, a denture cleansing tablet, a chewing gum, or a solid lozenge or the like.

Some embodiments provide a method of treating a disease or condition of the oral cavity comprising applying to the oral cavity surface of a subject in need thereof, of a composition as described herein. Other embodiments provide for the use of a composition as described herein for the manufacture of a medicament for treating a disease or condition of the oral cavity. In some embodiments, the disease or condition of the oral cavity is selected from oral malodor, plaque, gingivitis and periodontal disease.

In some embodiments, the present invention provides compositions and methods for reducing the presence of microorganisms in the oral cavity of a subject in need thereof.

In some embodiments, the compositions as described herein comprise one or more components which have an active oral hygiene function or provide a supporting function and do not interfere with the function of the active components. Examples of active components are tooth whiteners, antibacterial agents, abrasives or polishing materials, desensitizing agents, and the like. Examples of supporting components include surfactants, sweetening agents, preservatives, humectants, thickeners, and the like.

Quinone

As used herein, the term "quinone" means a cyclohexadiene-1,4-dione, or any similar compound containing two or more C—O groups in an unsaturated ring. A quinone may be present in the form of a hydroquinone (hydroxyquinone), in which one or more of the C=O groups is instead present as a C—OH group, or as a radical in which one or more of the C=O groups is present as C—O*. It may be present as a mixture of two or more of these forms, for instance as an equilibrium mixture of a benzoquinone and its corresponding hydroquinone.

The two C=O groups or C—OH groups of a (hydro) quinone may be positioned ortho, meta or para to one another, preferably either ortho or para, more preferably para as in p-benzoquinone (cyclohexadiene-1,4-dione) or the corresponding para-substituted hydroquinone HO-Ph-OH.

The quinone may for instance be a benzoquinone (by which is meant an optionally substituted cyclohexadiene dione, typically a cyclohexadiene-1,4-dione or cyclohexadiene-1,2-dione) or its corresponding hydroquinone, by which is meant a compound having an optionally substituted unsaturated 6-membered carbon ring, typically a phenyl ring, substituted with two or more —OH groups. In some embodiments, the quinone is an optionally substituted hydroquinone. As mentioned above, a hydroquinone may be present in the form of a radical in which one or more of the C—OH groups exists as C—O*.

Such compounds may be substituted with one or more other groups such as those selected from alkyl groups (in particular $C_1$ to $C_6$ or $C_1$ to $C_4$ alkyl groups, for instance methyl, ethyl, isopropyl or t-butyl groups); alkoxy groups (in particular $C_1$ to $C_6$ or $C_1$ to $C_4$ alkoxy groups such as methoxy or ethoxy); halides such as fluorides, chlorides or bromides; nitro groups —$NO_2$; and amine groups —$NR_2$ (where each R is independently either hydrogen or hydrocarbyl), in particular $NH_2$. The quinone may in particular be an alkyl-substituted hydroquinone or an alkyl-substituted benzoquinone. It may include up to four such substituents, but in particular may be mono- or di-substituted with such groups.

In a formulation according to the invention, the quinone is selected from the group consisting of unsubstituted benzoquinones (in particular p-benzoquinone), unsubstituted hydroquinones (in particular p-hydroquinone), alkyl-substituted benzoquinones and alkyl-substituted hydroquinones. In certain cases it may be preferred for the quinone not to be an unsubstituted hydroquinone.

In some embodiments, the quinone is either an alkyl-substituted benzoquinone or an alkyl-substituted hydroquinone, or a mixture of an alkyl-substituted benzoquinone and its corresponding hydroquinone. In other embodiments, the quinone is an alkyl-substituted hydroquinone.

A hydroquinone may be substituted with one or more alkyl groups. An alkyl group may be either a straight or a branched chain alkyl group. It may be or contain cycloalkyl moieties. It may contain for instance from 1 to 12 carbon atoms, preferably from 1 to 10, more preferably from 1 to 8. Particularly preferred alkyl groups are those selected from $C_1$ to $C_6$ alkyl groups, more preferably $C_1$ to $C_5$ alkyl groups, yet more preferably $C_1$ to $C_4$ alkyl groups, for instance methyl, ethyl, iso-propyl or t-butyl groups.

An alkyl group may be attached to a carbon atom of the cyclohexyl ring or to an oxygen atom (thus replacing the hydrogen atom of a hydroxyl group on the cyclohexyl ring). In some embodiments, it is attached to a carbon atom.

In some embodiments, the hydroquinone is substituted with up to six alkyl groups. In some embodiments, the hydroquinone is substituted with up to four alkyl groups. In other embodiments, the hydroquinone is a mono- or di-alkyl hydroquinone. In yet other embodiments, the hydroquinone is a mono-alkyl hydroquinone.

The hydroquinone may be substituted with one butyl group, which is preferably present at the 2 position; it may however be substituted with more than one butyl group, for instance two or three or four or even five. A butyl group is preferably a t-butyl group.

The hydroquinone may be substituted with two butyl groups, which preferably occupy the 2 and 5 positions. Again the butyl groups are preferably t-butyl groups.

Instead or in addition, the hydroquinone may be substituted with one hexyl group, which is preferably an O-substituted hexyl group for instance replacing the hydrogen atom of a 1-hydroxy group. The hydroquinone may however be substituted with more than one hexyl group, for instance two or three or even four. A hexyl group is preferably a straight chain hexyl group.

Instead or in addition, the hydroquinone may be substituted with one methyl group, which may for example be present at the 2 or the 5 position; it may however be substituted with more than one methyl group, for instance two or three or four or even five. It may for instance be substituted with three methyl groups, which are preferably present at the 2, 3 and 5 positions.

Instead or in addition, the hydroquinone may be substituted with one propyl group, suitably an iso-propyl group, which is preferably present at the 2 position. The hydroquinone may however be substituted with more than one propyl group, for instance two, three, four or even five. A propyl group is again suitably an iso-propyl group.

Instead or in addition, the hydroquinone may be substituted with one, two, three, four or even five ethyl groups.

Instead or in addition, the hydroquinone may be substituted with one, two, three or even four pentyl (preferably t-amyl) groups.

In particular the hydroquinone may be substituted with three methyl groups and one hexyl group, the hexyl group preferably replacing the hydrogen atom of a 1-hydroxy group and the three methyl groups preferably occupying the 2, 3 and 5 positions.

The term "hydroquinone" is not intended to embrace phenols, which have only one —OH group attached to a six-membered hydrocarbon ring.

Such compounds may be substituted with one or more alkyl groups, in particular $C_1$ to $C_6$ or $C_1$ to $C_4$ alkyl groups, for instance methyl, ethyl, isopropyl or t-butyl groups. Instead or in addition, they may be substituted with one or more halo groups. They are not generally substituted with other, non-alkyl and non-halo substituents, in particular alkoxyl groups such as methoxyl groups.

The quinone may be either an alkyl-substituted benzoquinone or an alkyl-substituted hydroquinone, or a mixture of an alkyl-substituted benzoquinone and an alkyl-substituted hydroquinone. More preferably it is an alkyl-substituted hydroquinone.

In an alkyl-substituted hydroquinone, an alkyl substituent may be attached to a carbon atom of the cyclohexyl ring or to an oxygen atom (thus replacing the hydrogen atom of a hydroxyl group on the cyclohexyl ring). In some embodiments, it is attached to a carbon atom.

In an embodiment the hydroquinone may be substituted with three methyl groups and one hexyl group, the hexyl group preferably replacing the hydrogen atom of a hydroxyl group and the three methyl groups preferably occupying the 2, 3 and 5 positions.

The hydroquinone may be substituted with one methyl and one iso-propyl group, which preferably occupy the 5 and the 2 positions respectively.

In particular the hydroquinone may be substituted with just one t-butyl group, which is preferably present at the 2 position. Alternatively the hydroquinone may be substituted with two butyl groups, which preferably occupy the 2 and 5 positions. In both cases the butyl groups are preferably t-butyl groups.

In some cases it may be preferred for the hydroquinone not to be a $C_6$ to $C_9$ alkyl-substituted resorcinol, in particular n-hexylresorcinol.

A halo-substituted hydroquinone may be substituted with up to four halo groups, more preferably up to three halo groups, but in particular may be a mono- or di-halo hydroquinone. A halo group may be for example either fluoro, chloro, bromo or iodo, suitably either chloro or fluoro, more suitably chloro. A hydroquinone may be substituted with one or more halo groups and in addition with one or more alkyl groups of the type described above.

An alkyl- or halo-substituted hydroquinone may be selected from the group consisting of 2-t-butyl-p-hydroquinone (TBHQ), 2,5-di-t-butyl-p-hydroquinone, 2,5-di-t-pentyl-p-hydroquinone, 2-isopropyl-p-hydroquinone, 2-ethyl-di-hydroquinone, 2-methyl-p-hydroquinone, 4-hexyl resorcinol and mixtures thereof. In cases it may be thymohydroquinone, which is a para-hydroquinone substituted at the 2-position with an isopropyl group and at the 5-position with a methyl group. In cases it may be 2,3-difluoro-/>>-hydroquinone. It may be selected from the group consisting of TBHQ, 2,5-di-t-butyl-p-hydroquinone, 2-ethyl-p-hydroquinone, 2-methyl-p-hydroquinone, 2,5-di-t-pentyl-p-hydroquinone, thymohydroquinone, 4-hexyl resorcinol, 2,3-difluoro-p-hydroquinone and mixtures thereof. It may in particular be TBHQ, i.e., a para-hydroquinone substituted at the 2 position with a t-butyl group.

An alkyl-substituted benzoquinone may be substituted with one or more alkyl groups, an alkyl group being as defined above. In some embodiments, substituents on a benzoquinone will be attached to carbon atoms of the cyclohexyl ring.

A benzoquinone may be substituted with up to four alkyl groups, but in particular may be a mono- or di-alkyl benzoquinone, preferably the former.

Such a benzoquinone is preferably substituted with one methyl group, which is preferably present at either the 2 or the 5 position; it may be substituted with more than one methyl group, for instance two or three or even four.

Instead or in addition, the benzoquinone is preferably substituted with one propyl group, which is preferably present at the 2 position; it may be substituted with more than one propyl group, for instance two or three or even four. A propyl group is preferably an iso-propyl group.

In particular the benzoquinone may be substituted with one methyl and one iso-propyl group, which preferably occupy the 5 and 2 positions respectively.

The benzoquinone may be substituted with one butyl group (for instance at the 2 position), or with more than one (for instance two, three or four) butyl groups. A butyl group is preferably a t-butyl group.

The benzoquinone may be substituted with two butyl groups, either or preferably both of which is a t-butyl group. These may for instance occupy the 2 and 5 positions, in particular where the benzoquinone is a para-benzoquinone. They may alternatively occupy the 3 and 5 positions, in particular where the benzoquinone is an ortho-benzoquinone.

Instead or in addition, the benzoquinone is preferably substituted with one ethyl group, which is preferably present at the 2 position; it may be substituted with more than one ethyl group, for instance two or three or even four.

Instead or in addition, the benzoquinone may be substituted with one, two, three or even four pentyl (preferably t-amyl) groups.

Instead or in addition, the benzoquinone may be substituted with one, two, three or even four hexyl groups.

A halo-substituted benzoquinone may be substituted with up to four halo groups, more preferably up to three halo groups, but in particular may be a mono- or di-halo hydroquinone. A halo group may be for example either fluoro, chloro, bromo or iodo, suitably either chloro or fluoro, more suitably chloro. A benzoquinone may be substituted with one or more halo groups and in addition with one or more alkyl groups of the type described above.

An alkyl- or halo-substituted benzoquinone may be selected from the group consisting of 2-t-butyl-p-benzoquinone (also known simply as t-butyl benzoquinone, or TBBQ), 2,5-di-t-butyl-p-benzoquinone, 2-ethyl-p-benzoquinone, 2-methyl-p-benzoquinone and mixtures thereof. In cases it may be thymoquinone, which is a para-benzoquinone substituted at the 2-position with an iso-propyl group and at the 5-position with a methyl group. It may be 2-chloro-5-methyl-p-benzoquinone. It may be selected from the group consisting of TBBQ, 2-ethyl-p-benzoquinone, 2-methyl-p-benzoquinone, thymoquinone, 2-chloro-5-methyl-p-benzoquinone and mixtures thereof. It may in particular be TBBQ.

In an embodiment of the invention, the quinone is an alkyl-substituted benzoquinone, hydroquinone or mixture thereof. In another embodiment, it is selected from the group consisting of TBHQ, TBBQ and mixtures thereof.

In an embodiment of the invention it may be preferred for the quinone not to be thymoquinone or thymohydroquinone.

In the present context an alkyl- or halo-substituted quinone may be present in the form of a dimer, oligomer or polymer, the monomer unit of which is an alkyl- or halo-substituted quinone as defined above. It may be in the form of a pharmaceutically acceptable (which term includes acceptable for veterinary use) derivative, for example a salt, complex or solvate or a so-called "prodrug" form or protected form which reverts to an active form of the relevant compound at an appropriate time on or after administration. Preferably, however, the quinone is present in the form of a single, underivatised quinone molecule.

A quinone used in a formulation prepared according to the invention, in particular thymoquinone, dithymoquinone or thymohydroquinone, is ideally used in the form of the isolated quinone (whether naturally or synthetically derived, preferably the latter) rather than as part of a plant extract containing a number of different materials.

In some embodiments, the quinones for use according to the invention are those selected from TBHQ, TBBQ and mixtures thereof. In some embodiments, the quinone is TBHQ.

The antimicrobial activity of any of the ingredients described herein may be assessed in a conventional manner, for instance using the tests described in the examples below.

In some embodiments, the quinone is present at a concentration of about 0.001 to about 10% w/w, about 0.005 to about 5% w/w, about 0.01 to about 1% w/w, or about 0.05% w/w, of the composition. In some embodiments, the quinone is present at a concentration of about 1 to about 500 ppm, about 10 ppm to about 100 ppm, about 12 ppm, about 25 ppm to about 75 ppm, or about 50 ppm. In some embodiments, the quinone is present in the composition at a concentration of about 50 ppm.

For oral delivery, the quinone may be formulated in dosage forms—for example tablets or capsules—containing 2 mg or greater, preferably 5 or 10 or 20 mg or greater, of the active substance. Such dosage forms may contain up to 250 mg, or in cases up to 100 mg, of the active substance, for instance from about 2 to 250 mg or from about 10 to 100 mg.

Antimicrobial

Non-limiting examples of antimicrobial compounds, such as for example phenolic compounds, include 4-allylcatechol, p-hydroxybenzoic acid esters including benzylparaben, butylparaben, ethylparaben, methylparaben and propylparaben, 2-benzylphenol, butylated hydroxyanisole, butylated hydroxytoluene, capsaicin, carvacrol, creosol, eugenol, guaiacol, halogenated bisphenolics including hexachlorophene and bromochlorophene, 4-hexylresorcinol, 8-hydroxyquinoline and salts thereof, salicylic acid esters including menthyl salicylate, methyl salicylate and phenyl salicylate, phenol, pyrocatechol, salicylanilide, thymol, triclosan and triclosan monophosphate. The antimicrobial phenolic compound may be in one aspect a halogenated diphenylether, for example triclosan, triclosan monophosphate or 2,2'-dihydroxy-5,5'-dibromodiphenylether.

Other suitable antimicrobial agents include without limitation copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like. A further illustrative list of useful antimicrobial agents is provided in U.S. Pat. No. 5,776,435 to Gaffar et al., incorporated herein by reference.

In some embodiments, at least one of the one or more antimicrobial agents is present at a concentration of about 0.005% to about 10% w/w, about 0.05% to about 5% w/w, about 0.1 to about 2% w/w, or about 0.3% w/w, of the composition. In other embodiments, at least one of the one or more antimicrobial agents is present in the composition at a concentration effective to deliver about 0.025 to about 10,000 ppm, about 0.05 to about 3000 ppm, about 2500 ppm, about 100 ppm to about 2000 ppm, about 200 ppm to about 1000 ppm, about 0.5 to about 200 ppm, about 1 to about 500 ppm, about 1 ppm, about 10 to about 200 ppm, about 150 ppm, about 50 to about 100 ppm, about 75 ppm, about 78 ppm. In some embodiments, at least one of the one or more antimicrobial agents is present at a concentration of greater than about 2500 ppm.

Compositions

In some embodiments, the compositions described herein comprise an orally acceptable vehicle or carrier. In some embodiments, the vehicle is prepared to target a desired site and/or time of delivery of the formulation. It may for instance target the formulation to the gums or teeth or other areas within the oral cavity. It may delay or otherwise control release of the formulation over a particular time period.

A formulation prepared according to the invention may contain standard excipients and/or other additives known for use in oral care, pharmaceutical or veterinary formulations. Examples include flavorings, antioxidants, preservatives, stabilizers, gelling agents and surfactants; and others found in "Oral Hygiene Products and Practice", 1988, supra.

In some embodiments, the vehicle might include a humectant. Suitable humectants include glycerol, sorbitol and polyethylene glycol, and in particular mixtures thereof. A polyethylene glycol humectant may for example have a molecular weight range of from 200 to 1000 or from 400 to 800, such as about 600. Humectants may be present in amounts from about 1.0% to about 75.0% by weight of the dentifrice composition. In some embodiments, the humectant is present in the amount of about 10 to 30% by weight. In other embodiments, the humectant is present in the amount of about 15 to 25% by weight. In further embodiments, the humectant is present in the amount of about 22% by weight. In some embodiments, the humectant is glycerol.

Suitable thickeners for use in toothpaste formulations include natural and synthetic gums and colloids such as carrageenan, xanthan gum and sodium carboxymethyl cellulose, as well as gum tragacanth; starch; polyvinyl pyrrolidone; cellulosic thickeners such as hydroxyethyl propyl cellulose, hydroxybutyl methyl cellulose, hydroxypropyl methyl cellulose, hydroxyethyl cellulose and water soluble salts of cellulose ethers such as sodium carboxymethyl cellulose or sodium carboxymethyl hydroxyethyl cellulose; and carboxyvinyl polymers. Suitable inorganic thickeners include colloidal silica, colloidal magnesium aluminium silicate, finely divided silica and synthetic hectorite. Mixtures of thickeners may also be used.

Suitable surfactants for use in the compositions as described herein may be anionic, nonionic, cationic, zwitterionic, amphoteric or ampholytic. In some embodiments, the surfactant is anionic. Examples of suitable anionic surfactants include higher alkyl sulfates such as sodium lauryl sulfate, and higher fatty acid esters of 1,2 dihydroxy propane sulphonate. In some embodiments, the surfactant is sodium lauryl sulfate. Other suitable surfactants for use in the compositions according to the invention are known in the art and may be found in McCutcheon's Detergents and Emulsifiers.

In some embodiments of the present invention, the composition is a toothpaste. In some embodiments, the toothpaste contains an abrasive or polishing agent. Suitable such agents include siliceous materials (including gels and precipitates, such as precipitated amorphous hydrated silicas, aluminium silicate, zirconlure silicate, silica gel and colloidal silica); carbonates and bicarbonates such as calcium carbonate and sodium bicarbonate; phosphates such as sodium metaphosphate, potassium metaphosphate, tricalcium phosphate, dicalcium orthophosphate dehydrate, calcium phosphate dihydrate, anhydrous dicalcium phosphate, calcium pyrophosphate, calcium polymetaphosphate, magnesium orthophosphate, trimagnesium phosphate and insoluble sodium polymetaphosphate; alumina trihydrate; calcined alumina; bentonite; complex amorphous alkali metal aluminosilicates; and resinous abrasive materials such as particulate condensation products of urea and formaldehyde. Mixtures of such polishing agents may also be used. The abrasive or polishing agent should not excessively abrade tooth enamel or dentin. In some embodiments, the abrasive is a silica abrasive.

Where a formulation prepared according to the invention takes the form of a mouthwash or dentifrice, it may for example contain a water/alcohol (e.g. water/ethyl alcohol) solution and optionally one or more other ingredients selected for example from flavorings, sweeteners, humectants, surfactants, emulsifiers if necessary and mixtures thereof. Suitable humectants include those described above, in particular glycerol and sorbitol. One or more additional antibacterial agents may also be included.

Suitable fluoride ion sources include water soluble fluorides such as water soluble alkali metal or alkaline earth metal fluorides, for example sodium, potassium and barium fluorides (in particular alkali metal fluorides); copper fluorides, such as cuprous fluoride; stannous fluoride; fluorosilicates such as sodium or ammonium fluorosilicate; fluorozirconates such as sodium or ammonium fluorozirconate; monofluorophosphates such as sodium or potassium monofluorophosphate; mono-, di- and tri-aluminium fluorophosphates; and fluorinated pyrophosphates such as fluorinated sodium calcium pyrophosphate. In some embodiments, the fluoride ion source is sodium monofluorophosphate.

Where the oral composition of the present invention is a solution or a liquid such as a mouthwash, the orally acceptable carrier is typically a water-alcohol mixture. Generally, the weight ratio of water to alcohol is in the range of from about 3:1 to 20:1 and preferably from about 4:1 to 10:1. In some embodiments, the alcohol is ethanol or isopropanol.

The compositions of this invention may also contain a desensitizing agent such as strontium chloride, potassium nitrate or sodium citrate-citric acid, which may be used in an amount from about 0.5% w/w to about 10% w/w.

In some embodiments, the quinone is TBHQ and the antimicrobial is stannous chloride. In other embodiments, the quinone is TBHQ and the antimicrobial is zinc citrate. In further embodiments, the quinone is TBHQ and the antimicrobial is zinc oxide. Still further embodiments provide compositions wherein the quinone is TBHQ and the antimicrobial is CPC. Yet further embodiments provide compositions comprising TBHQ and the antimicrobial is tetrahydrocurcumin.

In some embodiments the composition is a dual-phase or two-phase mouthwash composition, wherein the quinone is present in a first phase; and the one or more antimicrobial agents is present in a second phase.

As used herein, "inflammation" or "inflammatory condition" generally refers to a localized protective response elicited by injury or destruction of tissues, which serves to destroy, dilute, or sequester both the injurious agent and the injured tissue. In the acute form, it may be characterized by pain, heat, redness, swelling, and loss of function. Chronic inflammation is a slow process and primarily characterized by the formation of new connective tissue. Chronic inflammation is often a continuation of acute inflammation or a prolonged low-grade form of inflammation (such as that associated with periodontitis or gingivitis) and usually causes permanent tissue damage. Histologically, inflammation involves a complex series of events, including dilation of arterioles, capillaries, and venules, with increased permeability and blood flow; exudation of fluids, including plasma proteins, and leukocytic migration into the inflammatory locus. Inflammation corresponds to enhanced levels of pro-inflammatory cellular mediators, or substances that are released from cells, for example, as the result of the interaction of an antigen with an antibody or by the action of antigen with a sensitized lymphocyte.

In certain embodiments, when the oral composition is contacted with the oral tissue, it provides an analgesic effect on the inflamed oral tissue, thereby reducing sensations of pain and sensitivity in the oral tissue in the mammalian subject. In certain embodiments, the contacting of the oral care composition to the inflamed oral tissue is repeated at regular intervals.

Thus, in some embodiments the compositions described herein can be applied to sites of inflamed oral tissue at a concentration that reduces the production of one or more inflammatory cellular mediators. In various embodiments, the compositions described herein independently or simultaneously inhibit formation, or reduce expression, of pro-inflammatory mediators, for example, IL-1b, IL-6, PGE2 and TNF-α. Each respective mediator generally has a different mechanism in the pathogenesis of a disease.

Thus, in certain embodiments the compositions described herein can offset the innate effects of bone resorption and inhibition of bone formation as a result of over production and activity of cellular mediator molecules. In this manner, certain embodiments of the present invention provide methods for reducing alveolar bone loss, tooth loss and damage to mandibular bone as a result of trauma and/or infection in patients experiencing inflammation.

As recognized by those skilled in the art, complete suppression of cellular mediators could be detrimental to the mammalian subject, and in accordance with certain embodiments of the present invention, the production of cytokines is not entirely repressed. Thus, in various embodiments, the compositions described herein prevent the over-expression of one or more inflammatory mediators (which prevents an intrinsic mechanism for chronic disease), but still permits sufficient production of certain desirable mediator molecules (which are pleiotropic) to maintain homeostasis and normal cellular functions at basal levels.

Sources of oral tissue inflammation include, but are not limited to, bacterial infection, surgery, localized injury, trauma or necrosis, various systemic origins, or non-disease related etiologies such as overly aggressive oral hygiene practices or inappropriate dental hygiene practices. Non limiting examples of oral diseases, conditions, and disorders associated with enhanced activity of cellular mediators of inflammation include gingivitis, periodontitis, stomatitis, exfoliation of teeth due to neutropenia, endodontic pathoses and its sequela, acute and chronic ulceration of the oral mucosa, acute necrotizing ulcerative gingivitis, osteoclast/ondontoclast mediated resorptive legions, dental caries, delayed wound healing, periodontal bone damage and acute and chronic osteomyelitis of the mandibular bone.

Some embodiments provide methods of treating or preventing a disease or condition of the oral cavity comprising applying to an oral cavity surface of a subject in need thereof, the composition of any one of the foregoing claims. In some embodiments, the disease or condition of the oral cavity is an inflammatory disease or condition. In some embodiments, the inflammatory disease or condition of the oral cavity is selected from gingivitis, periodontitis, stomatitis, exfoliation of teeth due to neutropenia, endodontic pathoses and its sequela, acute and chronic ulceration of the oral mucosa, osteoclast/ondontoclast mediated resorptive lesions, dental caries, delayed wound healing, periodontal bone damage and acute and chronic osteomyelitis of the mandibular bone. In further embodiments, the gingivitis is acute necrotizing ulcerative gingivitis.

Further embodiments provide for the use of any of the compositions described herein for the manufacture of a medicament for use in a method for treating or preventing a disease or condition of the oral cavity.

The invention is further described in the following examples. The examples are merely illustrative and do not in any way limit the scope of the invention as described and claimed.

EXAMPLES

Example 1

TBHQ and a series of actives were tested in single species of *A. viscosus* biofilm assay. The data described in Tables 2 and 3 (below) is reported as the Biofilm Eradication Concentration ($BEC_{50}$) which is the lowest concentration at which greater than 50% reduction in biofilm biomass is observed relative to control. The data described in Tables 2 demonstrates that TBHQ at a concentration of 50 ppm does not provide a greater than 50% reduction in biofilm biomass; but, TBHQ at a concentration of 50 ppm provides an unexpected increase in the antimicrobial activity of zinc citrate, stannous chloride, tetrahydrocurcumin, CPC and triclosan.

TABLE 2

| Active | $BEC_{50}$ of Active Alone (ppm) | $BEC_{50}$ of Active + 50 ppm TBHQ (ppm) |
|---|---|---|
| TBHQ (50 ppm) | Not measurable | N/A |
| Zinc Citrate | 78.1 | 19.5 |
| Stannous chloride | 156.3 | 39 |
| Tetra-hydrocurcumin | >2500 | 1.22 |
| Cetylpyridinium chloride | 0.97 | <0.03 |
| Triclosan | 0.49 | <0.03 |

The data described in Table 3 demonstrates that TBHQ at a concentration of 12.5 ppm does not provide a greater than 50% reduction in biofilm biomass; but, TBHQ at a concentration of 12.5 ppm provides an unexpected increase in the antimicrobial activity of zinc oxide.

TABLE 3

| | BEC50 |
|---|---|
| TBHQ (12.5 ppm) | Not measurable |
| Zinc oxide slurry (1:1 water) | 9.76 |
| Zinc oxide slurry + TBHQ (12.5 ppm) | 1.22 |

Example 2

Exemplary compositions of the present invention are described below in Tables 4 and 5. These compositions can be prepared according to known methods for preparing oral care compositions. For example, a carrier can be prepared by combining, inter alia, appropriate amounts of humectant, surfactant, flavor, and water in a mixer. The desired amounts of quinone and antibacterial agent can then be added to the carrier.

The composition described in Table 4 (below) is an example of a toothpaste formulation according to some embodiments of the present invention.

TABLE 4

| Ingredient | w/w % |
|---|---|
| Polyethylene glycol | 1-5 |
| Sodium fluoride | 0.1-0.5 |
| Tetrasodium pyrophosphate | 0.1-1 |
| Sodium saccharin USP | 0.1-0.5 |
| Water | 5-30 |
| Sodium CMC | 0.1-1 |
| Humectant | 30-60 |
| Abrasive | 0-25 |
| Sodium lauryl sulfate | 0.5-2 |
| Flavor | 0.1-2 |
| Quinone | 0.01-1 |
| Antibacterial agent | 0.1-2 |

The composition described in Table 5 (below) is an example of a dual-phase mouthwash formulation according to some embodiments of the present invention.

TABLE 5

| Ingredient | w/w % |
|---|---|
| First Phase | |
| Quinone | 0.001-0.05 |
| Sunflower Oil | qs |
| Second Phase | |
| Tetrapotassium pyrophosphate | 1.1-1.5 |
| Tetrasodium pyrophosphate | 0.4-0.5 |
| Antibacterial agent | 0.01-0.5 |
| Sodium saccharin | 0.005-0.05 |
| Sodium fluoride | 0.01-0.1 |
| Gantrez S-97 | 1.5-2.3 |
| Methyl paraben | 0.01-0.5 |
| Propyl paraben | 0.01-0.5 |
| Colorant | 0.0001-0.001 |
| Glycerin | 5-10 |
| Sorbitol solution (70%) | 2.5-10 |
| Propylene glycol | 5-8 |
| Polysorbate 20 | 1-1.5 |
| Flavor | 0.05-0.5 |
| Water | qs |

Example 3

The anti-inflammatory efficacy of TBHQ in neat solution against several inflammation cytokines was evaluated. Human fibroblast (HEPM) cells or human macrophage (U937) cells were used in these tests. Inflammation was triggered by Heat Killed *P. gingivalis* (HKPG). TBHQ at various doses was co-incubated with cells treated with HKPG, and the levels of inflammatory markers were observed.

Table 6 (below) describes data demonstrating the activity of TBHQ on PGE2, at various concentrations.

TABLE 6

| Sample ID | PGE2 level (pg/mL) |
|---|---|
| Untreated | 1579 |
| HKPG | 1743 |
| TBHQ 62.5 ppm | 764 |
| TBHQ 31.2 ppm | 1124 |
| TBHQ 15.6 ppm | 1249 |
| TBHQ 7.8 ppm | 1563 |
| TBHQ 3.9 ppm | 1327 |
| TBHQ 1.8 ppm | 1378 |
| TBHQ 0.9 ppm | 1323 |

Table 7 (below) describes data demonstrating the activity of TBHQ on IL-1b, IL-6 and TNF-α, at various concentrations.

TABLE 7

| Sample ID | IL-1b (pg/mL) | IL-6 (pg/mL) | TNF-α (pg/mL) |
|---|---|---|---|
| Untreated | 63 | 42 | 15 |
| HKPG | 85 | 1753 | 194 |
| TBHQ 1 ppm | 88 | 405 | 198 |
| TBHQ 10 ppm | 55 | 100 | 68 |
| TBHQ 100 ppm | 29 | 23 | 7 |

Each of the patents, patent applications and printed publications (including books) mentioned in this document are hereby incorporated by reference in their entirety.

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising:
a quinone selected from the group consisting of alkyl-substituted benzoquinones, halo-substituted benzoquinones, alkyl-substituted hydroquinones and halo-substituted hydroquinones; and
one or more antimicrobial agents selected from the group consisting of zinc citrate, zinc oxide, stannous chloride, tetrahydrocurcumin, cetylpyridinium chloride and triclosan
wherein the quinone is provided in an amount effective to provide a synergistic increase in antimicrobial activity, and wherein at least one of said one or more antimicrobial agents is present at a concentration of from about 0.025 ppm to about 50 ppm.

2. The composition of claim 1, wherein at least one of said one or more antibacterial agents is zinc oxide.

3. The composition of claim 1, wherein the quinone is selected from tert-butylhydroquinone, tert-butyl benzoquinone, and a mixture thereof.

4. The composition of claim 1, wherein the quinone is tert-butylhydroquinone.

5. The composition of claim 1, wherein the quinone is present at a concentration of from about 10 ppm to about 1000 ppm.

6. The composition of claim 1, wherein the quinone is present at a concentration of about 50 ppm.

7. The composition of claim 1, wherein the quinone is present at a concentration of about 12 ppm.

8. The composition of claim 1, wherein the composition is a dual-phase mouthwash, and wherein the quinone is present in a first phase; and the one or more antimicrobial agents is present in a second phase.

9. A method of treating or preventing a disease or condition of the oral cavity comprising applying to an oral cavity surface of a subject in need thereof, the composition of claim 1.

10. The method of claim 9, wherein the disease or condition of the oral cavity is an inflammatory disease or condition.

11. The method of claim 10, wherein the inflammatory disease or condition of the oral cavity is selected from gingivitis, periodontitis, stomatitis, exfoliation of teeth due to neutropenia, endodontic pathoses and its sequela, acute and chronic ulceration of the oral mucosa, osteoclast/ondontoclast mediated resorptive lesions, dental caries, delayed wound healing, periodontal bone damage and acute and chronic osteomyelitis of the mandibular bone.

12. The method of claim 11, wherein the gingivitis is acute necrotizing ulcerative gingivitis.

13. The composition of claim 5, wherein at least one of said one or more antibacterial agents is zinc oxide.

14. The composition of claim 13, wherein the quinone is selected from tert-butylhydroquinone, tert-butyl benzoquinone, and a mixture thereof.

15. The composition of claim 14, wherein the quinone is tert-butylhydroquinone.

* * * * *